United States Patent [19]
Habeeb et al.

[11] Patent Number: 5,160,644
[45] Date of Patent: Nov. 3, 1992

[54] LUBRICATING OIL CONTAINING O-ALKYL-N-ALKOXYCARBONYLTH- IONOCARBAMATE SALTS OF DIALKYLDITHIOPHOSPHORIC ACID (PNE-614)

[75] Inventors: Jacob J. Habeeb; Morton Beltzer, both of Westfield, N.J.

[73] Assignee: Exxon Research and Engineering Co., Florham Park, N.J.

[21] Appl. No.: 805,759

[22] Filed: Dec. 12, 1991

[51] Int. Cl.$^5$ ............... C10M 137/08; C10M 137/10
[52] U.S. Cl. .................. 252/32.7 E; 252/47.5; 252/400.22; 252/400.21
[58] Field of Search .............. 252/47.5, 32.7 E; 560/148

[56] References Cited

U.S. PATENT DOCUMENTS

| Re. 32,786 | 11/1988 | Fu et al. | 560/148 |
| 4,556,483 | 12/1985 | Fu et al. | 560/148 |
| 4,659,853 | 4/1987 | Fu et al. | 560/148 |

FOREIGN PATENT DOCUMENTS 376889  7/1990  European Pat. Off. .

OTHER PUBLICATIONS

CA 114(14):125696k.
Smalheer et al., "Lubricant Additives", 1967.

*Primary Examiner*—Ellen McAvoy
*Attorney, Agent, or Firm*—John W. Ditsler; James H. Takemoto

[57] ABSTRACT

The addition of an O-alkyl-N-alkoxycarbonylthionocarbamate salt of dialkyldithiophosphoric acid to a lubricating oil imparts antiwear and/or antioxidation performance to the oil.

10 Claims, No Drawings

LUBRICATING OIL CONTAINING O-ALKYL-N-ALKOXYCARBONYLTHIONOCARBAMATE SALTS OF DIALKYLDITHIOPHOSPHORIC ACID (PNE-614)

BACKGROUND OF THE INVENTION

1. Field of the Invention

This invention relates to a lubricating oil composition having good antiwear and/or antioxidation performance due to the presence of an O-alkyl-N-alkoxy-carbonylthionocarbamate salt of dialkyldithiophosphoric acid.

2. Description of Related Art

Engine lubricating oils require the presence of additives to protect the engine from wear. For almost forty years, the principal antiwear additive for engine lubricating oils has been zinc dialkyldithiophosphate (ZDDP). Typically, ZDDP must be used in concentrations of about 1.0 to 1.4 wt.% or greater to be effective in reducing wear. However, phosphates may cause the deactivation of emission control catalysts used in automotive exhaust systems. In addition, ZDDP alone does not provide the enhanced antiwear protection necessary in oils used to lubricate today's small, high performance engines. Furthermore, ZDDP also adds to engine deposits which cause increased oil consumption and increased particulate and regulated gaseous emissions. Accordingly, reducing or eliminating the amount of phosphorus-containing additives (such as ZDDP) in the oil would be desirable.

O-alkyl-N-alkoxycarbonylthionocarbamates and their method of preparation are known (see U.S Pat. No. 4,659,853, the disclosure of which is incorporated herein by reference). In addition, copending patent application U.S. Ser. No. 805,757 filed on the same date herewith discloses that O-alkyl-N-alkoxycarbonylthionocarbamates impart improved antiwear and/or friction reducing performance to lubricating oils. However, neither the patent nor the application mention the use of O-alkyl-N-alkoxycarbonylthionocarbamate salts of dialkyldithiophosphoric acid in a lubricating oil.

SUMMARY OF THE INVENTION

In one embodiment, this invention concerns a lubricating oil composition which comprises
(a) a lubricating oil basestock, and
(b) an O-alkyl-N-alkoxycarbonylthionocarbamate salt of dialkyldithiophosphoric acid having the formula

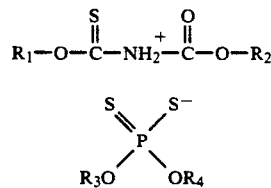

where
$R_1$ and $R_2$ are each an alkyl group, an aryl group, an alkaryl group, an arylalkyl group, or substituted derivatives thereof, containing from 1 to 20 carbon atoms, and
$R_3$ and $R_4$ are selected from hydrogen and a hydrocarbyl group containing from 1 to 28 carbon atoms.

In another embodiment, this invention concerns a method for improving the antiwear and/or antioxidation performance of an internal combustion engine by operating the engine with a lubricating oil containing the salts described above. In yet another embodiment, this invention concerns an additive concentrate containing the above-described salts that is suitable for blending with a lubricating oil.

DETAILED DESCRIPTION OF THE INVENTION

This invention requires a lubricating oil basestock and an oil soluble 0-alkyl-N-alkoxycarbonylthionocarbamate salt of dialkyldithiophosphoric acid (DDP).

In general, the lubricating oil will comprise a major amount of a lubricating oil basestock (or base oil) and a minor amount of an 0-alkyl-N-alkoxycarbonylthionocarbamate. If desired, other conventional lubricating oil additives may be present in the oil as well.

The lubricating oil basestock can be derived from natural lubricating oils, synthetic lubricating oils, or mixtures thereof. In general, the lubricating oil basestock will have a kinematic viscosity ranging from about 5 to about 10,000 cSt at 40° C., although typical applications will require an oil having a viscosity ranging from about 10 to about 1,000 cSt at 40° C.

Natural lubricating oils include animal oils, vegetable oils (e.g., castor oil and lard oil), petroleum oils, mineral oils, and oils derived from coal or shale.

Synthetic oils include hydrocarbon oils and halo-substituted hydrocarbon oils such as polymerized and interpolymerized olefins (e.g. polybutylenes, polypropylenes, propylene-isobutylene copolymers, chlorinated polybutylenes, poly(1-hexenes), poly(1-octenes), poly(1-decenes), etc., and mixtures thereof); alkylbenzenes (e.g. dodecylbenzenes, tetradecylbenzenes, dinonylbenzenes, di(2-ethylhexyl)benzene, etc.); polyphenyls (e.g. biphenyls, terphenyls, alkylated polyphenyls, etc.); alkylated diphenyl ethers, alkylated diphenyl sulfides, as well as their derivatives, analogs, and homologs thereof; and the like.

Synthetic lubricating oils also include alkylene oxide polymers, interpolymers, copolymers and derivatives thereof wherein the terminal hydroxyl groups have been modified by esterification, etherification, etc. This class of synthetic oils is exemplified by polyoxyalkylene polymers prepared by polymerization of ethylene oxide or propylene oxide; the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof (e.g., the acetic acid esters, mixed $C_3$–$C_8$ fatty acid esters, and $C_{13}$ oxo acid diester of tetraethylene glycol).

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, pentaerythritol monoethylether, and the like.

Silicon-based oils (such as the polyakyl-, polyaryl-, polyalkoxy-, or polyaryloxy-siloxane oils and silicate oils) comprise another useful class of synthetic lubricating oils. These oils include tetraethyl silicate, tetraisopropyl silicate, tetra-(2-ethylhexyl) silicate, tetra-(4-methyl-2-ethylhexyl) silicate, tetra(p-tert-butylphenyl) silicate, hexa-(4-methyl-2-pentoxy)-disiloxane, poly(methyl)-siloxanes and poly(methylphenyl) siloxanes, and the like. Other synthetic lubricating oils include liquid esters of phosphorus-containing acids (e.g., tricresyl phosphate, trioctyl phosphate, diethyl ester of decylphosphonic acid), polymeric tetrahydrofurans, polyalphaolefins, and the like.

The lubricating oil may be derived from unrefined, refined, rerefined oils, or mixtures thereof. Unrefined oils are obtained directly from a natural source or synthetic source (e.g., coal, shale, or tar sands bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

The O-alkyl-N-alkoxycarbonylthionocarbamate salts of dialkyldithiophosphoric acid used in this invention are oil soluble and have the general formula:

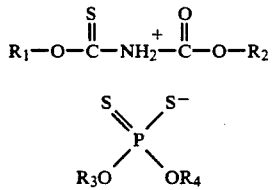

where

R$_1$ and R$_2$ are each an alkyl group (straight, branched, or cyclic), an aryl group, an alkaryl group, an arylalkyl group, or substituted derivatives thereof, containing from 1 to 20 carbon atoms, and R$_3$ and R$_4$ are selected from hydrogen and a hydrocarbyl group containing from 1 to 28 carbon atoms, preferably an alkyl group containing from 3 to 12 carbon atoms. R$_3$ and R$_4$ may be the same or different.

Preferably, R$_1$ is a branched alkyl group containing from 1 to 15 carbon atoms, more preferably from 2 to 12 carbon atoms, and most preferably from 4 to 8 carbon atoms. Preferably, R$_2$ is a straight alkyl group containing from 1 to 15 carbon atoms, more preferably from 2 to 8 carbon atoms, and most preferably from 2 to 4 carbon atoms. R$_1$ and R$_2$ may be the same or different, but together should contain a sufficient number of carbon atoms such that the O-alkyl-N-alkoxycarbonylthionocarbamate is soluble in the oil. Preferably, R$_2$ will be different from R$_1$. Examples of suitable substituted groups in R$_1$ and R$_2$ include alkyl, aryl, hydroxy, alkylthio, amido, amino, keto, ester groups, mercapto, thio, and the like, with hydroxy in the form of a hindered dialkyl phenol being most preferred.

Examples of O-alkyl-N-alkoxycarbonylthionocarbamates that can be used in this invention include O-isobutyl-N-ethoxycarbonylthionocarbamate, O-isobutyl-N-dodecyloxycarbonylthionocarbamate, O-(3,5-di-t-butyl-4-hydroxybenzyl)-N-ethoxycarbonylthionocarbamate, O-2-hydroxyethyl-N-ethoxycarbonylthionocarbamate, O-2-(bis-N-2-hydroxyethyl) aminoethyl-N-ethoxycarbonylthionocarbamate, 0-2-aminoethyl-N-ethoxycarbonylthionocarbamate, O-methylene-N-ethoxycarbonylthionocarbamate dimer, or mixtures thereof, and the like, with O-isobutyl-N-ethoxycarbonylthionocarbamate being most preferred.

A preferred O-alkyl-N-alkoxycarbonylthionocarbamate salt of DDP that can be used in this invention is O-alkyl-N-alkoxycarbonylthionocarbamate diisooctyldithiophosphate, with O-isobutyl-N-ethoxycarbonylthionocarbamate diisooctyldithiophosphate being most preferred.

The amount of O-alkyl-N-alkoxycarbonylthionocarbamate salts of DDP used in this invention need be only an amount which is necessary to impart antiwear and/or antioxidation performance to the oil, i.e., a wear and/or oxidation reducing amount. Typically, however, the concentration of the O-alkyl-N-alkoxycarbonylthionocarbamate salts in the lubricating oil will range from about 0.1 to about 1 wt. %, although larger amounts could be used. Preferably the amount will range from about 0.1 to about 0.5 wt. %, of the oil.

If desired, other additives known in the art may be added to the lubricating oil basestock. Such additives include dispersants, other antiwear agents, other antioxidants, corrosion inhibitors, detergents, pour point depressants, extreme pressure additives, viscosity index improvers, friction modifiers, and the like. These additives are typically disclosed, for example, in "Lubricant Additives" by C. V. Smalhear and R. Kennedy Smith, 1967, pp. 1–11 and in U.S. Pat. No. 4,105,571, the disclosures of which are incorporated herein by reference.

O-isobutyl-N-ethoxycarbonylthionocarbamates and DDP are commercially available from one or more vendors. As such, the salts of this invention can be easily prepared by neutralizing the O-alkyl-N-alkoxycarbonylthionocarbamates with the DDP.

The O-alkyl-N-alkoxycarbonylthionocarbamate salts of DDP can be added directly to the lubricating oil. Often, however, they can be made in the form of an additive concentrate to facilitate their handling and introduction into the oil. Typically, the concentrate will contain a suitable organic diluent and from about 10 to about 90 wt. %, preferably from about 30 to about 80 wt. %, of the additives. Suitable organic diluents include mineral oil, naphtha, benzene, toluene, xylene, and the like. The diluent should be compatible (e.g. soluble) with the oil and, preferably, substantially inert.

A lubricating oil containing the O-alkyl-N-alkoxycarbonylthionocarbamate salts of DDP described above can be used in essentially any application where wear and/or oxidation protection is required. Thus, as used herein, "lubricating oil" (or "lubricating oil composition") is meant to include automotive lubricating oils, industrial oils, gear oils, transmission oils, and the like. In addition, the lubricating oil composition of this invention can be used in the lubrication system of essentially any internal combustion engine, including automobile and truck engines, two-cycle engines, aviation piston engines, marine and railroad engines, and the like. Also contemplated are lubricating oils for gas-fired engines, alcohol (e.g. methanol) powered engines, stationary powered engines, turbines, and the like.

This invention may be further understood by reference to the following example, which includes a preferred embodiment of this invention.

EXAMPLE

Antiwear and Antioxidation Performance of O-alkyl-N-alkoxycarbonylthionocarbamate Salts of DDP Four Ball Wear tests and oxidative differential scanning calorimetry (DSC) tests were performed to determine the effectiveness of O-alkyl-N-alkoxycarbonylthionocarbamate salts of DDP in reducing wear and oxidation in various lubricating oils. The Four Ball test used is described in detail in ASTM method D-2266, the disclosure of which is incorporated herein by reference. In this test, three balls are fixed in a lubricating cup and an upper rotating ball is pressed against the lower three balls. The test balls utilized were made of AISI 52100 steel with a hardness of 65 Rockwell C (840 Vickers) and a centerline roughness of 25 mm. Prior to the tests, the test cup, steel balls, and all holders were washed with 1,1,1 trichloroethane. The steel balls subsequently were washed with a laboratory detergent to remove any solvent residue, rinsed with water, and dried under nitrogen.

The Four Ball wear tests were performed at 100° C., 60 kg load, and 1200 rpm for 45 minutes duration. After each test, the balls were washed and the Wear Scar Diameter (WSD) on the lower balls measured using an optical microscope. Using the WSD's, the wear volume (WV) was calculated from standard equations (see Wear Control Handbook, edited by M. B. Peterson and W. O. Winer, p. 451, American Society of Mechanical Engineers [1980]). The percent wear reduction (% WR) for each oil tested was then calculated using the following formula:

$$\% \, WR = \left[ 1 - \frac{WV \text{ with additive}}{WV \text{ w/o additive}} \right] \times 100$$

In the DSC test, a test sample is heated at a programmed rate and its temperature rise is compared to that of an inert reference. If the sample undergoes an exothermic or endothermic reaction or phase change, the event and magnitude of the heat effects are monitored and recorded. The temperature at which the exothermic reaction due to oxidation by atmospheric oxygen starts is an indication of the oxidation stability of an oil. The higher the temperature, the more stable the oil. The rate of temperature increase selected was 5° C./minute in the temperature range 50° C. to 300° C.

The results of these tests and calculations are shown in Table 1 below:

TABLE 1

| Oil | CTCB:DDP Wt % (4) | WV mm$^3$ × 10$^4$ | WR % | DSC Oxidation Onset, °C. |
|---|---|---|---|---|
| (1) | 0.0 | 558 | 0.0 | 210 |
|  | 0.1 | 77 | 86.2 | 248 |
|  | 0.5 | 20 | 96.4 | 265 |
|  | 1.0 | 23 | 95.9 | 262 |
| (2) | 0.0 | 388 | 0.0 | 224 |
|  | 0.1 | 214 | 44.8 | 245 |
|  | 0.5 | 14 | 96.4 | 243 |
|  | 1.0 | 14 | 96.4 | 247 |
| (3) | 0.0 | 508 | 0.0 | 267 |
|  | 0.1 | 12 | 97.6 | 270 |
|  | 0.5 | 12 | 97.6 | 272 |
|  | 1.0 | 5 | 99.0 | 268 |

(1) Oil 1 is a solvent extracted, dewaxed, hydrofined neutral basestock having a viscosity of 32 centistokes at 40° C.

(2) Oil 2 is a commercially available SAE 10W30 automotive engine oil having a maximum absolute viscosity of 3500 centipoises at −20° C. and a kinematic viscosity between 9.3 and 12.5 cSt at 100° C. Oil 2 contains 80 wt. % of Oil 1 as basestock additives including detergents, dispersants, VI improvers, antioxidants, antifoaming agents, etc., but no ZDDP.

(3) Oil 3 is a commercially available SAE 10W30 automotive engine oil having a maximum absolute viscosity of 3500 centipoises at −20° C. and a kinematic viscosity between 9.3 and 12.5 cSt at 100° C. Oil 3 contains 9.5 wt. % of Oil 1, 17.8 wt. % of a basestock having a kinematic viscosity of 129 cSt (or 600 SUS) at 40 C., 50 wt. % of a polyalphaolefin having a viscosity of 6 cSt (or 45 SUS) at 40° C., and 22.7 wt. % of the conventional lubricating oil additives mentioned in (2) above, but no ZDDP.

(4) The additive tested was O-isobutyl-N-ethoxycarbonylthionocarbamate diisooctyldithiophosphate.

The data in Table 1 show that O-alkyl-N-alkoxycarbonylthionocarbamate salts of dialkyldithiophosphoric acid impart excellent antiwear and antioxidation performance to lubricating oils. Thus, the use of O-alkyl-N-alkoxycarbonylthionocarbamate salts of dialkyldithiophosphoric acid allows the formulation of a lubricating oil having effective antiwear and antioxidation performance in the absence of ZDDP.

The additives of this invention can also be used to form a lubricating oil containing a reduced amount of phosphorus-containing compounds (e.g. less than 0.1, less than 0.05, or even less than 0.01 wt. % phosphorus).

What is claimed is:

1. A lubricating oil composition which comprises
   (a) a lubricating oil basestock, and
   (b) an O-alkyl-N-alkoxycarbonylthionocarbamate salt of dialkyldithiophosphoric acid having the formula

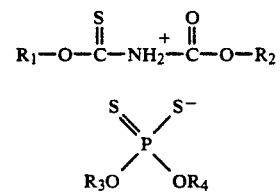

where
  $R_1$ and $R_2$ are each an alkyl group, an aryl group, an alkaryl group, an arylalkyl group, or substituted derivatives thereof, containing from 1 to 20 carbon atoms, and
  $R_3$ and $R_4$ are selected from hydrogen and a hydrocarbyl group containing from 1 to 28 carbon atoms.

2. The composition of claim 1 wherein $R_1$ is a straight chained alkyl group.

3. The composition of claim 2 wherein $R_2$ is a straight chained alkyl group.

4. The composition of claim 3 wherein at least one of $R_3$ and $R_4$ is an alkyl group containing from 4 to 12 carbon atoms.

5. The composition of claim 1 wherein the salt is O-alkyl-N-alkoxycarbonylthionocarbamate diisooctyldithiophosphate.

6. The composition of claim 5 wherein the salt is O-isobutyl-N-ethoxycarbonylthionocarbamate diisooctyldithiophosphate.

7. A method of improving the antiwear performance, antioxidation performance, or antiwear and antioxidation performance of an internal combustion engine which comprises operating the engine with a lubricating oil comprising a major amount of the lubricating oil basestock and a minor amount of the O-alkyl-N-alkoxycarbonylthionocarbamate salt of dialkyldithiophosphate of claim 1.

8. The method of claim 7 wherein the salt is -alkyl-N-alkoxycarbonylthionocarbamate diisooctyldithiophosphate.

9. An additive concentrate suitable for blending with lubricating oils to provide a lubricating composition having antiwear and/or antioxidation performance which comprises an organic diluent and from about 10 to about 90 wt. % of the O-alkyl-N-alkoxycarbonylthionocarbamate salt of dialkyldithiophosphoric acid of claim 1.

10. The concentrate of claim 9 wherein the organic diluent is mineral oil, naphtha, benzene, toluene, or xylene.

* * * * *